United States Patent [19]

Willner et al.

[11] Patent Number: 4,821,739
[45] Date of Patent: Apr. 18, 1989

[54] DEVICE AND METHOD FOR TESTING FOR A CORSET OR SPINAL ORTHOSE

[75] Inventors: Stig Willner, Malmö; Gert Karlsson, Helsingborg, both of Sweden

[73] Assignee: Camp Scandinavia AB, Helsingborg, Sweden

[21] Appl. No.: 133,126
[22] PCT Filed: Nov. 24, 1986
[86] PCT No.: PCT/SE86/00535
   § 371 Date: Sep. 4, 1987
   § 102(e) Date: Sep. 4, 1987
[87] PCT Pub. No.: WO87/03191
   PCT Pub. Date: Jun. 4, 1987

[30] Foreign Application Priority Data

Nov. 25, 1985 [SE] Sweden .................... 8505547

[51] Int. Cl.⁴ ............................................. A61B 5/10
[52] U.S. Cl. ................................. 128/774; 128/781; 128/78
[58] Field of Search ............... 128/781, 774, 78, 75, 128/69, 87 B; 33/511, 512, 515; 623/38, 901

[56] References Cited

U.S. PATENT DOCUMENTS

| | | | |
|---|---|---|---|
| 2,760,486 | 8/1956 | Ward | 128/78 |
| 2,835,247 | 5/1958 | Stabholz | 128/78 |
| 3,605,731 | 9/1971 | Tigges | 128/78 |
| 3,889,664 | 6/1975 | Heuser et al. | 128/78 |
| 3,926,182 | 12/1975 | Stabholz | 128/78 |
| 4,559,933 | 12/1985 | Batard et al. | 128/78 |

FOREIGN PATENT DOCUMENTS

| | | |
|---|---|---|
| 0107305 | 5/1984 | European Pat. Off. |
| 0144528 | 6/1985 | European Pat. Off. |
| 115594 | 12/1900 | Fed. Rep. of Germany |
| 2429582 | 2/1980 | France ................. 128/781 |
| 362199 | 12/1973 | Sweden |
| 1443891 | 7/1976 | United Kingdom |

OTHER PUBLICATIONS

Search Report—International Application, PCT/SE86/00535.

Primary Examiner—Edward M. Coven
Assistant Examiner—J. P. Lacyk
Attorney, Agent, or Firm—Ladas & Parry

[57] ABSTRACT

The present invention relates to a device and a method for testing out a spinal orthose or corset on a patient, whereby the device consists of a frame (2), which is width and height adjustable, a back beam (3), a back plate (16) with a support means (17, 18, 19, 22, 23, 25) belonging thereto and an abdominal plate (26). The device (1) is fixed on the back of the patient by adjusting the frame to the correct height and width, whereafter the back plate is fixed in the correct position by means of the support means. The values measured in such a way are transferred to a corset blank by means of a measurement rod (36) (FIG. 1).

7 Claims, 2 Drawing Sheets

DEVICE AND METHOD FOR TESTING FOR A CORSET OR SPINAL ORTHOSE

FIELD OF THE INVENTION

The invention defines a device and a method for testing for a spinal orthose or corset for orthophedic use on back disorders.

PRIOR ART

Spinal orthoses or corsets of different shapes are of great use in medical therapy to relieve the pain of various back disorders and, in fact, are one of the most commonly prescribed technical facilities within the orthopedic field. About 50,000 corsets are prescribed annually in Sweden. By the expression "corsets" is henceforward intended its broadest meaning, i.e. cloth as well as plastic corsets (orthoses). Without any doubts they have any many times a good effect on different pain conditions in the loins, but often corsets are prescribed on uncertain indications, which entails that the patients with back disorders do not get the desired palliation of their pains and for this reason do not use the corset. It is therefore important to get as clear indications as possible from the beginning if a corset should be prescribed and moreover how it should be shaped. This should be done before the manufacture and delivery of the corset. This is not of the least economical importance, since the costs of corsets for medical use are high 50,000 corsets are ordinated yearly in Sweden at present.

The fact that corsets in many cases are of great importance for palliation of the suffering of patients with back disorders and for allowing increased mobility is evident. This is especially true when the back pain is related to a position or a movement, i.e. if the pain decreases or disappears in certain positions, e.g. when a patient is lying, sitting, or in a bent forward position. However, it is very important that the corset is specially shaped and adjusted for the patient in question, since different patients have different kinds of pain as well as different shapes of the back.

Today standard corsets of cloth or plastic with a certain prefabricated form of saddle support and abdominal pressure are used. However, it has been found that the patient at mechanically caused pain conditions in the loins, obtains a maximal palliation of pain with the corset only in a certain position of the loins. This entails that patients with a standard corset do not always obtain the desired palliation of their pains, by the fact that the corset is not correctly shaped and for this reason the patient does not use his corset.

Another reason for not using the corset is that sometimes the patients suffer from stomach pains, like catarrhal gastritis etc. and for this reason they cannot stand the abdominal pressure, which is necessary for supporting the back. Thus, these patients should have been dissuaded from using a corset.

Several investigations have been made to establish the results of corset treatment. In an investigation of Ahlgren S.A. and Hansen T "The use of lumbosacral corsets prescribed for low back pain", Prostheth, Ortop, 3nt, 2:101-104, 1978 it was found that around three fourths of the patients with back pains who had received corsets were using the same. Of the patients who four years later still suffered from back disorders two thirds used their orthos and they were of the opinion that they had more or less benefit from the use thereof.

In another publication of McKenzie A.R. and Lipscomb (1979) it was discovered that only 50 percent of the patients who were prescribed a corset stated a clear improvement.

The purpose of the corset treatment is greatly to allow a mobilization of the patient but still to avoid strain of the loins, i.e. to obtain painlessness.

Imaginable causes for lumbosacral pains have been previously discussed and the effect of the corset thereon have also been discussed in the literature, but are still not made clear. Imaginable facts which affect the effect of the corset on the condition of the illness are:
1. immobilization of the vertebral column
2. stabilization
3. decreased intradiscal pressure by means of increased intraabdominal pressure
4. increase of the intraspinal space by lordotisation of the loins.

Probably the cause could be found within several of these possibilities.

Patients with lumbago acuta are usually free from pain if keeping the back completely still and many patients with this kind of pain do also state an improvement when using a corset.

The stability of the back is above all determined by the muscles of the trunk. This is also affected by an increased intrathoral and intraabdominal pressure, which increases the load on the disks but which also stabilizes the vertebral column. The corset is assumed to increase the stability and many patients with symptoms of back sufficience become free of pain when using the same.

An object with the present invention is to provide a device, by means of which a correctly shaped corset can be manufactured. By means of this device it is possible to establish whether a corset on the whole can be expected to give any result and in that case how the corset should be shaped in order to give optimal result.

Another object with the present invention is to provide a method for for a corset, whereby the measurements which are measured by aid of the instrument simply can be transferred to a corset blank.

SUMMARY OF THE INVENTION

In order to overcome the above mentioned disadvantages and to achieve the objects stated a device for trying out a corset on a patient is provided according to the present invention, whereby the device comprises a frame, which surrounds the back of the patient and is width and height adjustable: an adjustable back beam attached to the frame; a back plate, which is movably attached to the back beam; an abdominal plate for distribution of the pressure against the abdomen of the patient, and a measurement rod for transferring the values set to a corset blank by aid of the frame, the back beam and the back plate.

Moreover, a method for trying for a corset on a patient is provided, whereby the height and width of the back of a patient are set by means of an adjustable frame; the elevation position of the saddle on the patient and the depth of the saddle is measured by means of an adjustable back beam and back plate coupled to the frame by means of an adjustable carrier device, and finally these measured values are transferred to a corset blank by a measurement rod.

BRIEF DESCRIPTION OF THE INVENTION

DETAILED SPECIFICATION OF THE INVENTION

Figure 1:
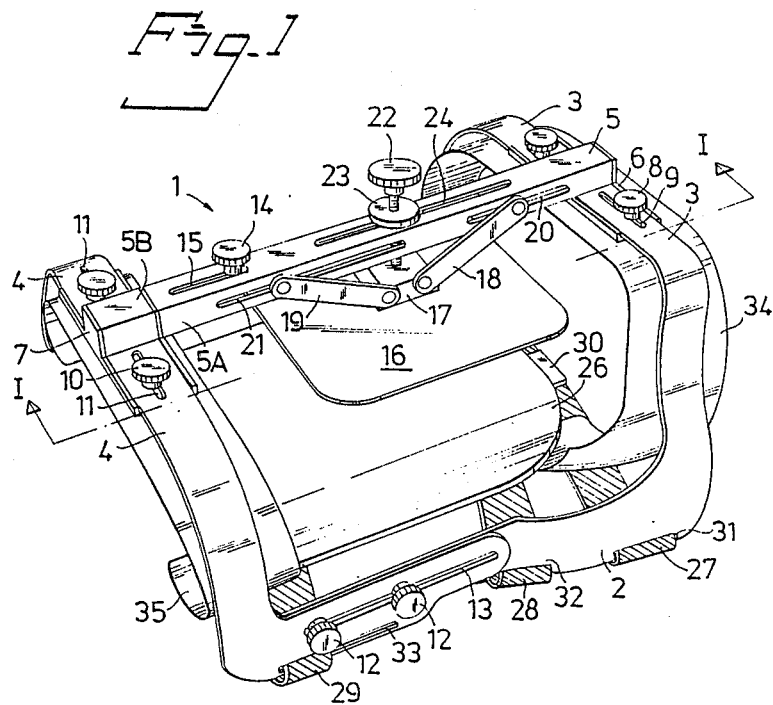
FIG. 1 is a perspective view, from behind, of an embodiment of the device according to the invention.

With regard especially to FIG. 1 an embodiment of a device 1 according to the invention is shown, which device comprises a frame 2, combined wth two lower clamps 3, two upper clamps 4, and a back beam 5. The upper and the lower clamps are angled so that they essentially follow the back with a smooth, straight portion and follow the side by means of a portion angled in relation to the straight portion. From the angled portion a straight portion runs downwardly along the side of the body. The back beam is at its upper end connected to the upper clamp 4 via a T-shaped portion 7, which in its turn is attached to and hold together the upper clamps 4. The lower end of the back beam is in a corresponding way attached to the lower clamps 3. Screws 8 are inserted in grooves 9 in the lower clamps 3 and the screws are threaded in the T-shaped portion 6. When the screws are not tightened the lower clamps 3 can be displaced laterally to a desired lower width for the device and thereafter be braced in position by means of the screws 8. in the same way the upper clamps 4 are attached to the upper T-shaped portion 7 of the back beam 5 with screws 10 in the grooves 11.

Those portions of the clamps 3 and 4 which run sideways are connected by means of a similar arrangement, two screws 12 are at each side threaded in the lower clamp 3 and pass through a groove 13 in the upper clamp in order to adjust the height of the device. For the purpose of adjusting the height the back beam 5 also consists of two telescopically connected portions 5A and 5B, whereby a screw 14 is threaded in the upper portion 5B and passes through a groove 15 in the lower portion 5A.

On the back beam 5 is arranged a unit for setting of the saddle support, comprising a back plate 16, manufactured by a material which shows flexibility as well as stability, e.g. plastic, which plate is attached to an insert 17. On each side of the insert 17 are positioned lower rods 18 and upper rods 19. The upper rods 19 are rotatably attached with a pin on each side of the insert 15 and extend from the insert and upwardly to grooves 21 in the side of the back beam, where they are attached at a through pin which runs in the grooves 21. The lower rods 18 are attached in the same way and extend from the insert and upwardly against the grooves 20.

Figure 2:
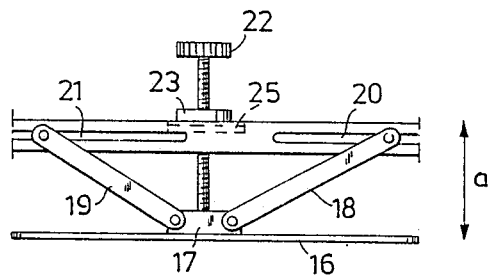
FIG. 2 is a detail view of the setting means for the device shown in FIG. 1, seen along line I—I in FIG. 1.

The depth of the saddle support, i.e. the distance a, in FIG. 2, between the back beam and the back plate 16, is adjusted by means of a screw 22, which is threaded in a plate 25 positioned inside the back beam and which passes through a fastener 23 on the upper side of the beam and through a groove 24 in the beam. The screw 22 is rotatably attached in the insert 17. The elevation level of the saddle support can be adjusted by displacement of the back plate along the back beam 5, whereby the screw 22 runs in the groove 24 and the rods 18, 19 run in the grooves 20, 21. A certain level is fixed by clasping the fastener 23 which is threaded to the screw 22.

Figure 3:
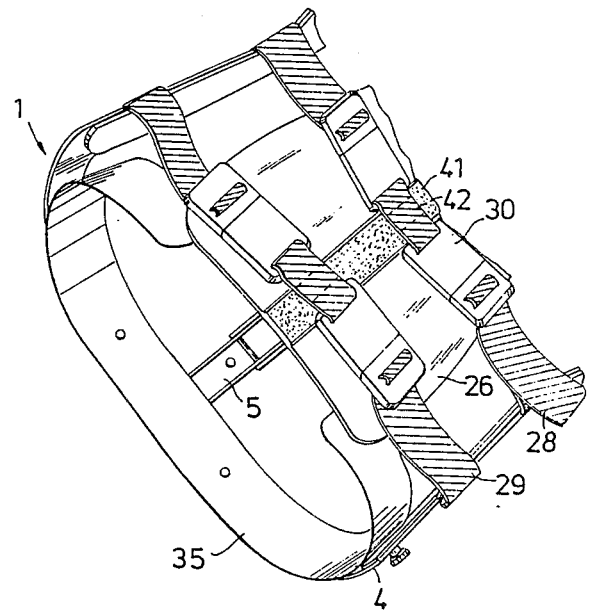
FIG. 3 is a perspective view of the embodiment shown in FIG. 1, seen from the front.

A certain abdominal pressure is provided by means of an abdominal pressure plate or abdominal plate 26, which by means of three straps 27, 28 and 29 are braced against the abdomen of the patient. This is best illustrated by FIG. 3, but also by FIG. 1. Each strap consists of two portions, which are connected with a buckle 30 and the abdominal plate 26 is removably attached to the straps by means of Velcro tapes. In FIG. 3 this attachment is i.a. shown between a longitudinal Velcro tape 41 on the abdominal plate and Velcro tapes 42 attached on the inner side of each strap. On the inner side of the abdominal plate are also suitably Velcro tapes (not shown) by means of which it is possible to attach a cushion or pelott (not shown) for the purposes of allowing an adjustment of the distribution and size of the abdominal pressure. The straps 27, 28 and 29 are attached in grooves 31, 32 and 33, respectively in the sides 3, 4 of the clamps. The upper clamps 33 are longer than the remaining grooves and have suitably a length which corresponds to the double width of the strap so that the upper strap 29 can be displaced and that the device thereby can be adjusted to the constitution of the patient.

The clamps 3 and 4 are furthermore provided with linings 34, 35, preferably of plastic which surrounds the back of the patient.

The linings 34, 35 protect the patient from direct contact with the metal frame and above all aim at giving the patient about the same feeling as a later corset will give. One of the very purposes of the present invention is—as exactly as possible—to imitate a corset, in order to be able to decide whether a corset is the correct ordination.

The device also comprises an measurement rod 36, which is constructed similar to the back beam 5 and which consists of two telescopically connected portions 36A and 36B, which can be fixed in relation to each other by aid of a screw 37. A measuring screw 38 is positioned in a groove throught the measurement rod and can be put in an optional along the measurement rod in the same way as the screw 22 on the back beam 5. By means of the measurement rod 36 the measures obtained via the frame 2, the back beam 5 and the back plate 16 with an adjustable support means is to be transferred to a corset blank. At the transfer the measurement rod is placed beside the back beam with support against the frame.

The device is used in the following way. The screws 8, 10, 12 and 14 are loosened and the back plate is screwed back against the screw 22 as far as possible. The device is thereafter placed on the back of the patient so that the curvature of the lower clamp 3 is steadily placed over the ilium (the christa edges). Thereupon the height is adjusted so that the upper clamps 4 will be positioned by the lower edge of the shoulder blades (scapula) but do not prevent its movement, whereby the elevation adjustment screws 12 and 14, respectively, are clamped.

Then the upper (4) and lower (3) clamps, respectively, are pressed together so that the sides of the clamps lie against the body, whereafter the side adjustment screws 8, 10 are fastened. Thereupon a suitable abdominal plate 26 is chosen and positioned with its lower portion resting on the pubic bone (pubis). Suitably at least two different abdominal plates are prepared; one for shorter patients and one for taller ones. If required, loose cushions can be placed inside the plate 26. Then the buckles of the straps 27, 28 and 29 are attached on the front of the Velcro tapes of the plate 26 and the straps are tightened so that the device steadily fits the body. Thereby the fastener 23 is, which is positioned in the back beam 5 is loosened, so that the plate can run freely in the groove 24. Now the centre of the back plate is placed above the area where the optimal effect of the pressure can be expected, usually in the maximal inclination (the vertex of the lordosis, whereupon the fastener 23 is clamped. Then the back plate 16 is screwed up until the patient experiences that the back is in the position where the pain is at a minimum or disappears. If the patient now is able to move from the front and backwards (anterio-posterio) in the device this means that the abdominal pressure is too low and extra cushions must then be inserted between the patient and the abdominal plate 26. By screwing out the back plate 16 so that it no longer rests against the back, the buckles are loosened in the front and a cushion is inserted. Thereupon the straps are fastened as tightly as the patient may accept and the back plate 16 is once more screwed on until the patient is out of pain. It is then controlled that the patient can no longer move anterio-posterio.

Figure 4:
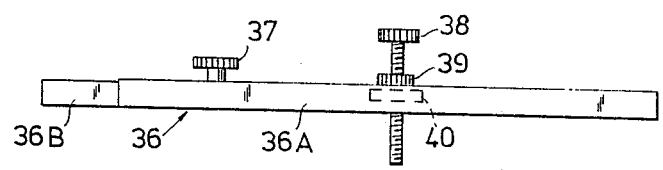
FIG. 4 is a view of a transfer instrument, which is used at the device according to the invention to transfer measured measurements.

When the correct shape for the corset to come has been measured and also checked with the patient that the corset will be accepted, the measured values should be transferred to a corset blank. This is made means of the measurement rod 36, which is shown in FIG. 4 and by means of which the position as well as the size of the inclination of the saddle is measured. After removing the device from the back of the patient, with the measured positions well fixed, the measurement rod is placed beside and adjacent the back beam 5. By means of the screw 37 the measurement rod is adjusted to the same length as the back beam 5. The measurement screw 38 is moved along with the measurement rod so that it will be at the same level as the screw 22 and the fastener 23 and thereupon the measurement screw is screwed up until it touches the back plate 16. With the iliac crest as a reference line the distance to the measurement screw 38 is then measured and a measurement of the level for the maximum inclination of the saddle is obtained, and its distance in relation to the reference line. These measurements are transferred to a corset blank. The width of the corset is chosen according to standards.

A suitable corset blank is chosen and a hole in the back of the corset blank is drilled, where the measurement screw 38 will pass and the measurement rod is placed against the rear side of the blank with the measurement screw 38 through the drilled hole. The saddle support can then be built-up by means of bars on the inner side of the corset to an exact level and inclination. Regarding the material for the device the frame is suitably made of aluminum, while the linings together with the back plate and the abdominal plate are suitably made of stiff, flexible plastic. However, other materials can be suitable. By aid of the described device it is thus possible to manufacture especially adjusted corsets for patients and also on a very early stage it can be decided whether a corset is the correct treatment in each individual case.

A better assistance can be given to those patients who are to be treated with corsets through the individual embodiment, and large costs are avoided due to erroneous ordinations of corsets. For the patients not to be treated with a corset the advantage is achieved that without any extra delay it is possible to change to another form of treatment.

In the specification above a preferred embodiment of the invention is defined, which, however, can be modified by a person skilled in the art. The invention is only restricted to the accompanying claims.

I claim:

1. A device for testing a patient for a spinal orthose or corset, the device comprising: a frame (1) for surrounding the back of a patient, the frame being width and height adjustable; an adjustable back beam (5) attached to the frame; a back plate (16) movably attached to the back beam (5); and an abdominal plate (26) attached to the frame (1) for distribution of pressure against the abdomen of the patient; in combination with a measurement rod (36) for transferring values set thereon by the frame (1), back beam (5) and back plate (16) to a corset blank; the frame (1) comprising two lower clamps (3) and two upper clamps (4), the clamps being adjustable in relation to each other for the width and height adjustment of the frame, the lower clamps (3) being attached to each other with screws (8) inserted in grooves (9) in the lower clamps, the upper clamps (4) being attached to each other with screws (10) inserted in grooves (11) in the upper clamps, and both the lower and upper clamps (3, 4) being attached to the adjustable back beam (5).

2. A device according to claim 1, characterized in that the back beam (5) consists of two telescopically connected portions (5A, 5B).

3. A device according to claim 1, characterized in that the back plate (16) is mounted inside the back beam (5) by means of an adjustable support means (17, 18, 19, 22, 23, 25) so that the back plate can be adjusted in an optional position along the back beam (5) and in a positioned displaced from the back beam.

4. A device according to claim 1, characterized in that the measurement rod (36) consists of two telescopically connected portions (36A, 36B).

5. A device according to claim 4, characterized in that the measurement rod moreover is equipped with adjustment means (37-40) for transfer of the set values of the back beam (5).

6. A method for testing a patient for a spinal orthose or corset, comprising:
providing a movable back plate on a back beam adjustably on a frame for surrounding the back of a patient's body;
measuring set elevation and depth position values of the back plate and beam relative to the frame with a measuring rod for determining corresponding elevation and depth positions of the saddle of the patient's back; and
transferring the set values to a corset.

7. A method according to claim 6, characterized in that the measurement device is placed on the frame alongside the back support whereby the transfer of the set values to the corset blank is made in such away that the length of the measurement device is adjusted so that it agrees with the length of the back support, the elevation level of the back plate and its position towards the body of the patient in relation to the back beam.

* * * * *